United States Patent [19]
Wall et al.

[11] Patent Number: 5,997,971
[45] Date of Patent: Dec. 7, 1999

[54] WOOD PRESERVATIVE WRAP

[75] Inventors: Wesley James Wall; Calvin Lee Michael Wall, both of Edmonton, Canada

[73] Assignee: Genics Inc., Spruce Grove, Canada

[21] Appl. No.: 08/908,096

[22] Filed: Aug. 11, 1997

[30] Foreign Application Priority Data

Jul. 21, 1919 [CA] Canada ................................. 2210941

[51] Int. Cl.⁶ ........................... B65D 65/28; B65D 73/00
[52] U.S. Cl. ............................ 428/43; 428/72; 428/166; 428/172; 428/178; 206/484; 206/484.2
[58] Field of Search ............................ 428/178, 72, 166, 428/172, 176, 541, 43, 906; 52/738.1; 206/484, 484.2; 47/24; 427/440; 405/231, 303

[56] References Cited

U.S. PATENT DOCUMENTS

| | | | |
|---|---|---|---|
| 4,731,267 | 3/1988 | Makus et al. | 428/35 |
| 4,779,735 | 10/1988 | Kelso et al. | 206/484 |
| 5,194,315 | 3/1993 | Itoh | 428/178 |
| 5,352,502 | 10/1994 | Fuller | 428/178 |
| 5,405,671 | 4/1995 | Kamin et al. | 428/178 |
| 5,491,008 | 2/1996 | Woó et al. | 428/182 |
| 5,591,263 | 1/1997 | Chin et al. | 118/200 |

*Primary Examiner*—Donald Loney
*Attorney, Agent, or Firm*—Anthony R. Lambert

[57] ABSTRACT

A wood preservative wrap includes a body divided by liquid impervious grid lines into a plurality of pockets filled with wood preservative. The body is trimmable along the grid lines without compromising the containment of the wood preservative.

11 Claims, 3 Drawing Sheets

WOOD PRESERVATIVE WRAP

FIELD OF THE INVENTION

The present invention relates to a wood preservative wrap for use in preserving wooden poles, posts, pilings, or any piece of wood with potential for decay.

BACKGROUND OF THE INVENTION

U.S. Pat. No. 4,731,267 which issued to Makus and Bennett in 1988 discloses a delivery system for wood preservative. The delivery system consists of a pouch filled with wood preservative chemical that is designed to be wrapped around a base of a pole. The pouch is slit to wrapping around a pole, in order to permit the wood preservative to leak out into the wood. The slits are sized to enable the wood preservative to treat the wood over a prolonged period of time.

This delivery system has been quite successful, but has some inherent problems. The pouch used must be of a size that fits the pole. If the pouch is too small to go around the entire circumference of the pole, the treatment is ineffective. If the pouch is too large, there is a danger that excess wood preservative chemicals will run down the pole and leach into the soils causing environmental damage. To ensure that the proper size is available, the pouch is available in sizes that start at 30 inches and increase in length by 6 inch increments up to 72 inches.

SUMMARY OF THE INVENTION

What is required is an improved form of wood preservative wrap.

According to the present invention there is provided a wood preservative wrap which includes a body divided by liquid impervious grid lines into a plurality of pockets filled with wood preservative. The body is trimmable along the grid lines without compromising the containment of the wood preservative.

The wood preservative wrap, as described above, avoids many of the problems inherent in the old pouch wrap. The old pouch wrap could not be trimmed, as it would compromise the containment of the wood preservative resulting in a loss of wood preservative into the soil. The wood preservative wrap, as described above, can be trimmed along the grid lines to suit any length that is desired. This results in less wastage, and obviates the need to carry a massive inventory of pouches of varying sizes. It is anticipated that the body will always be provided in strips well in excess of 12 feet and then trimmed to length as required. The length of the body gives rise to means for dispensing that are new in the industry. The body may be mounted upon a dispensing roll or arranged in a zig zag fashion within a dispensing container.

Although beneficial results may be obtained through the use of the wood preservative wrap, as described above, it is sometimes desirable to be able to cut around obstacles. Even more beneficial results may, therefore, be obtained when the grid lines include intersecting longitudinal grid lines and transverse grid lines. This permits any width to be accommodated as well as any length and enables rectangular sections to be removed in order to get around an obstacle. It also permits flaps to be created that can be slid under such obstacles as a conduit running up the pole.

Although beneficial results may be obtained through the use of the wood preservative wrap, as described above, there are advantages to be obtained when the wood preservative is in the form of a gel. When the wood preservative is in the form of a gel, the need for a wood preservative bearing substrate is eliminated, which reduces the cost of the produce. A gel is also easier to work with in any manufacturing process for forming a body having a plurality of wood preservative pockets, as described. The gel can serve as a conditioner for the pole, providing a moisture seal which repels water.

Although beneficial results may be obtained through the use of the wood preservative wrap, as described above, another problem experienced is ensuring that the body is correctly slit. If the slits are too small, an insufficient quantity of wood preservative will be administered to the pole. If the slits are too large, the treatment will not be released over time as intended and fracturing may occur creating large holes or gaps in the pouch. If the slits are too deep, the containment of the wood preservative is totally compromised, resulting leakage and a strong likelihood of soil contamination. Even more beneficial results may, therefore, be obtained when the body consists of a liquid impervious layer and a liquid pervious layer covered by a removable liquid impervious peel off layer. The body can then be made ready for use by simply removing the removable liquid impervious peel off layer to expose the liquid pervious layer through which wood preservative can pass. This eliminates the need for the wrap to be perforated at the time of application and takes the guess work out of making perforations sufficient in both quantity and size.

Although beneficial effects may be obtained through the use of the wood preservative wrap, as described above, it can be a nuisance carrying waste from remote locations for disposal. Even more beneficial results may, therefore, be obtained when the removable liquid impervious peel off layer is made of soil biodegradable material. This enables the removable liquid impervious peel off layer to be buried at the base of the pole after removal. This is extremely convenient as the application of a wood preservative wrap usually involves some excavation at a base of the pole.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
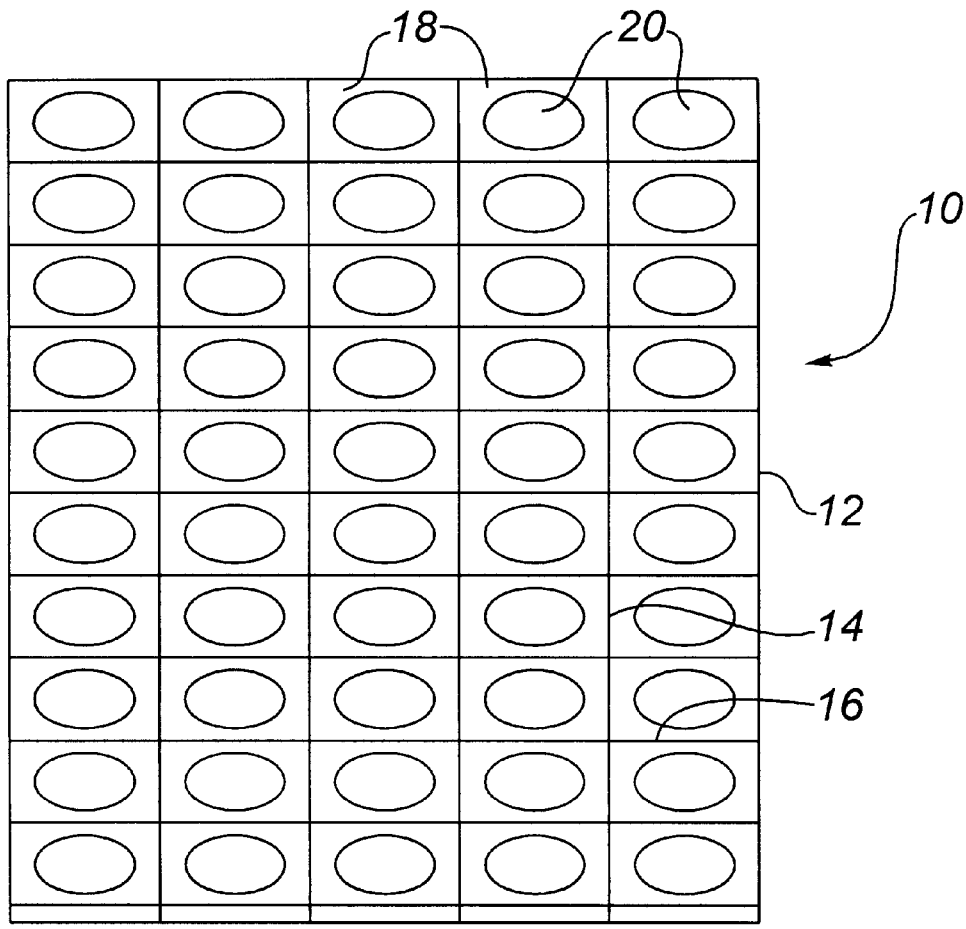
FIG. 1 is a top plan view of a wood preservative wrap constructed in accordance with the teachings of the present invention.

The preferred embodiment, a wood preservative wrap generally identified by reference numeral 10, will now be described with reference to FIGS. 1 through 5.

Figure 2:
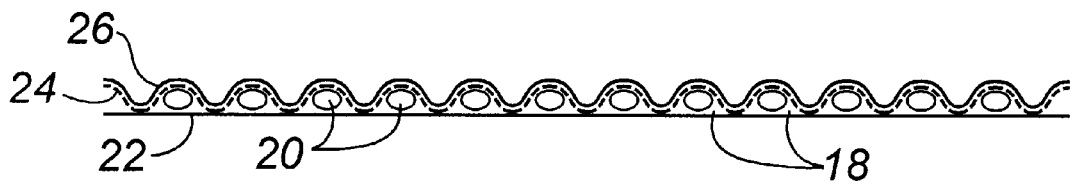
FIG. 2 is a side elevation view, in section, of the wood preservative wrap illustrated in FIG. 1.
Figure 3:
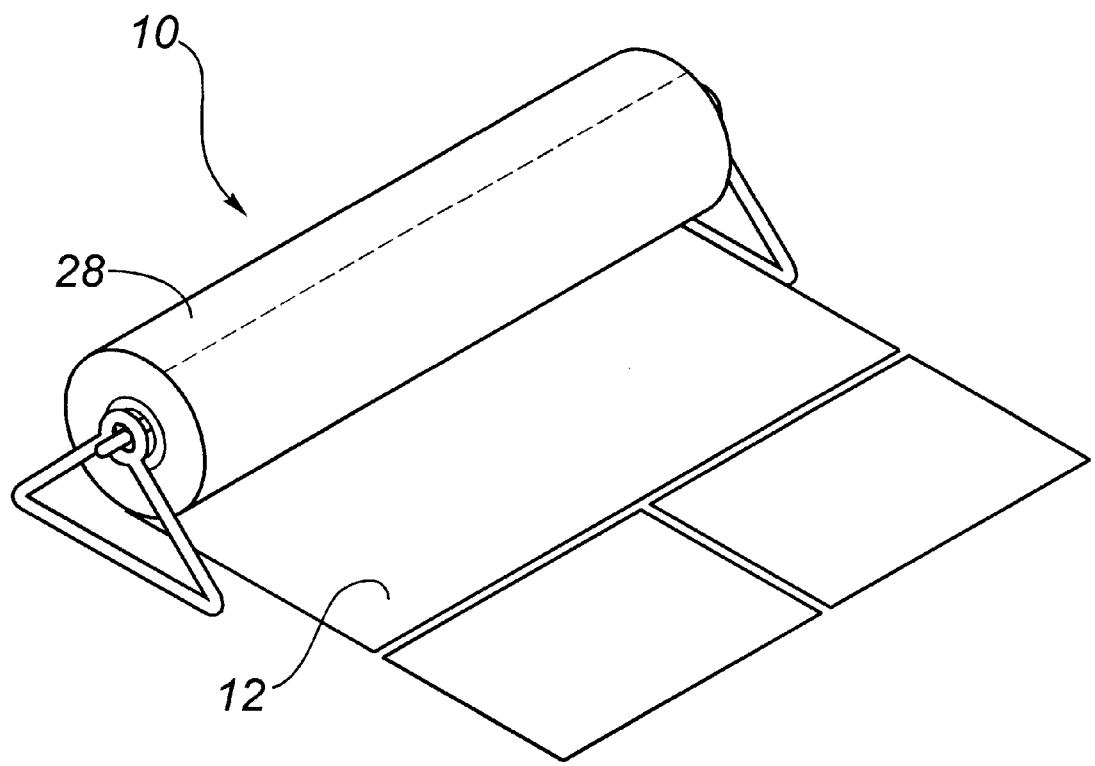
FIG. 3 is a side elevation view of the wood preservative wrap illustrated in FIG. 1, mounted on a dispensing roll.
Figure 4:
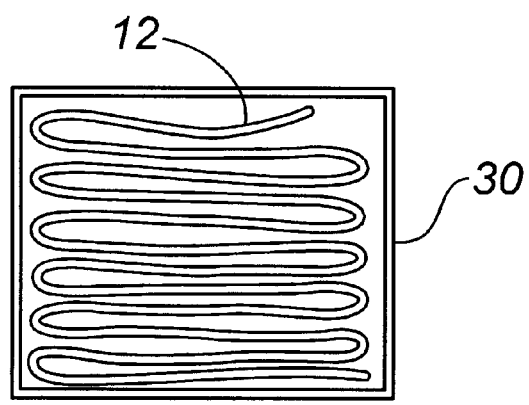
FIG. 4 is a side elevation view of the wood preservative wrap illustrated in FIG. 1, stored in a zig zag fashion in a dispensing box.

Referring to FIG. 1, wood preservative wrap 10 has an elongate body 12 divided by intersecting longitudinal grid lines 14 and transverse grid lines 16. Referring to FIG. 2, grid lines 14 and 16 are liquid impervious and serve to divide body 12 into a plurality of pockets 18 filled with a wood preservative gel 20. It is anticipated that body 12 will be made from a material such as polyethylene and grid lines 14 and 16 formed by heat sealing. Referring to FIG. 2, body 12 includes a liquid impervious layer 22 and a liquid pervious layer 24 covered by a removable liquid impervious peel off layer 26. In the absence of removable liquid impervious peel off layer 26, wood preservative gel 20 would tend to leak through liquid pervious layer 24. Body 12 is intended to be manufactured in lengths considerably longer than 12 feet. It is anticipated that typical length will be approximately 50 feet. Referring to FIG. 3, one preferred manner of dispensing contemplated is to mount body 12 upon a dispensing roll 28. Referring to FIG. 4, another preferred manner of dispensing contemplated is to fold body 12 in a zig zag fashion and place body in a box 30, in a manner similar to the way that computer paper is commonly dispensed. It is preferred that removable liquid impervious peel off layer 26 be made of soil biodegradable material.

Figure 5:
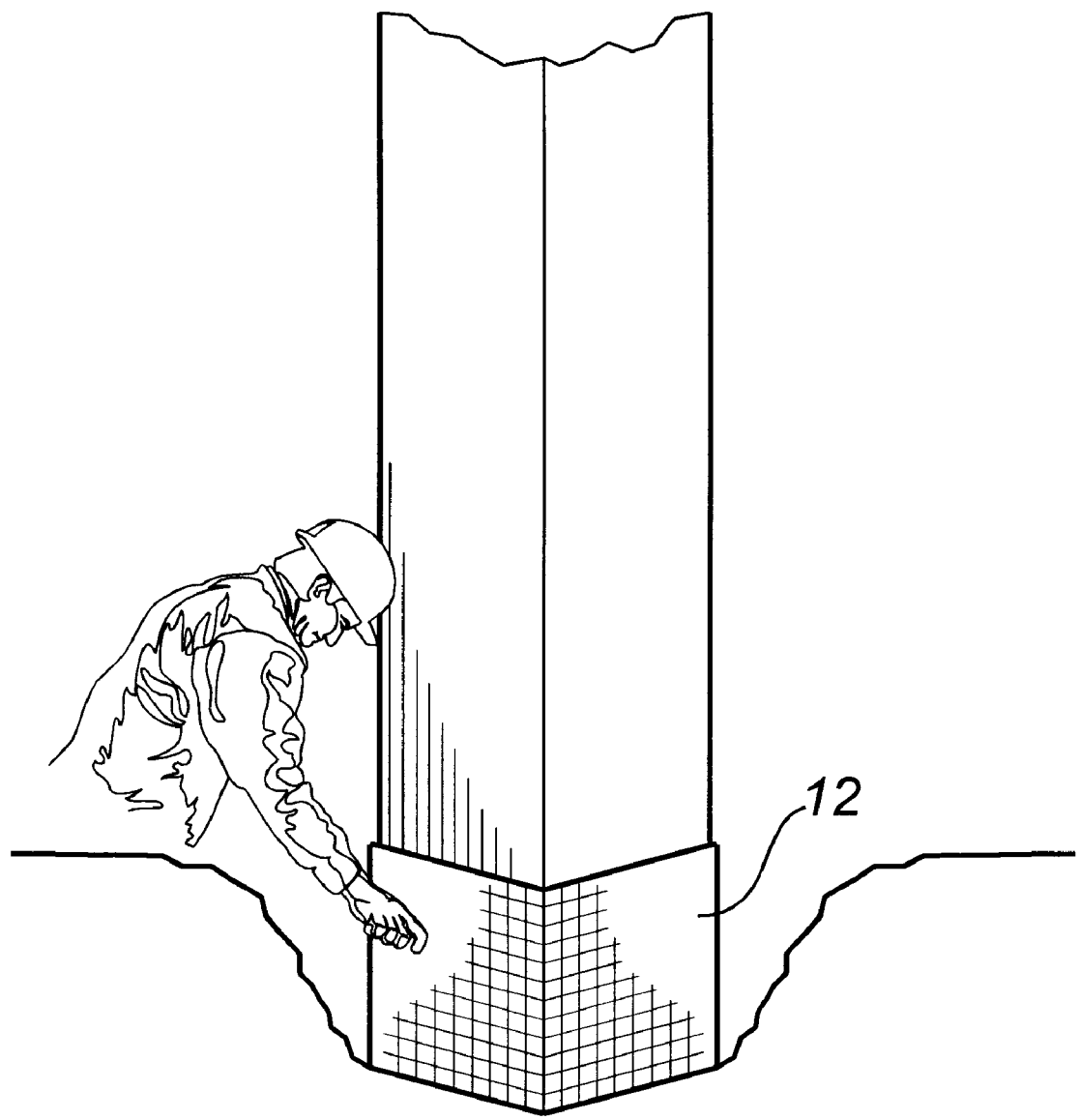
FIG. 5 is a perspective view of the wood preservative wrap illustrated in FIG. 1, in the process of treating a pole.

The use of wood preservative wrap 10 will now be described with reference to FIGS. 1 through 5. A required length of body 12 is taken off dispensing roll 28 as illustrated in FIG. 3 or drawn from box 30 as illustrated in FIG. 4. Referring to FIG. 5, body 12 is then cut to length along one of transverse grid lines 16, and trimmed as required to avoid obstacles along both longitudinal grid lines 14 and transverse grid lines 16. For example, there may be roots, underground cable, or underground bracing adjacent a base of the pole which must be avoided. As long as body 12 is only cut along grid lines 14 or 16, the containment of the wood preservative gel 20 is not compromised. Body 12 is then made ready for use by removing removable liquid impervious peel off layer 26 to expose liquid pervious layer 24 through which wood preservative gel 20 can pass. After removal, removable liquid impervious peel off layer 26 is buried at the base of the pole where it will degrade in the soil over time.

In some circumstances, for example when body 12 is overlying a conduit, it is desirable to leave a portion of liquid impervious peel off layer 26 adhered to liquid pervious layer 24. This prevents wood preservative gel 20 from going directly onto the conduit.

It will be apparent to one skilled in the art that modifications may be made to the illustrated embodiment without departing from the spirit and scope of the invention as hereinafter defined in the Claims.

The embodiments of the invention in which an exclusive property or privilege is claimed are defined as follows:

1. A wood preservative wrap, comprising:
    a liquid impervious body formed of at least two layers of pliant polymer plastic sheet material heat sealed together to form intersecting liquid impervious longitudinal grid lines and transverse grid lines which divide the body into a plurality of pockets filled with wood preservative, such that the body is trimmable along the grid lines without compromising the containment of the wood preservative.

2. The wood preservative wrap as defined in claim 1, wherein the body is of a length in excess of 12 feet.

3. The wood preservative wrap as defined in claim 2, wherein the body is mounted upon a dispensing roll.

4. The wood preservative wrap as defined in claim 2, wherein the body is folded in a zig zag fashion.

5. The wood preservative wrap as defined in claim 1, wherein the wood preservative is in the form of a gel.

6. The wood preservative wrap as defined in claim 1, wherein the body consists of a liquid impervious layer and a liquid pervious layer covered by a removable liquid impervious peel off layer, such that the body is made ready for use by removing the removable liquid impervious peel off layer to expose the liquid pervious layer through which wood preservative can pass.

7. The wood preservative wrap as defined in claim 6, wherein the removable liquid impervious peel off layer is made of soil biodegradable material, whereby the removable liquid impervious peel off layer may be buried after removal.

8. A wood preservative wrap, comprising:
    a body formed of at least two layers of pliant polymer plastic sheet material heat sealed together to form intersecting liquid impervious longitudinal grid lines and transverse grid lines which divide the body into a plurality of pockets filled with wood preservative gel, such that the body is trimmable along the grid lines without compromising the containment of the wood preservative;
    the body including a liquid impervious layer and a liquid pervious layer covered by a removable liquid impervious peel off layer, such that the body is made ready for use by removing the removable liquid impervious peel off layer to expose the liquid pervious layer through which wood preservative can pass.

9. The wood preservative wrap as defined in claim 8, wherein the body is mounted upon a dispensing roll.

10. The wood preservative wrap as defined in claim 8, wherein the body is folded in a zig zag fashion.

11. The wood preservative wrap as defined in claim 8, wherein the removable liquid impervious peel off layer is made of soil biodegradable material, whereby the removable liquid impervious peel off layer may be buried after removal.

* * * * *